(12) United States Patent
Kong et al.

(10) Patent No.: US 12,188,908 B2
(45) Date of Patent: Jan. 7, 2025

(54) INTEGRATED TRIAXIAL SHEAR AND SEEPAGE EXPERIMENTAL METHOD FOR HYDRATE-BEARING SEDIMENTS AND DEVICE THEREOF

(71) Applicant: Qingdao University of Technology, Qingdao (CN)

(72) Inventors: Liang Kong, Qingdao (CN); Yapeng Zhao, Qingdao (CN); Rui Xu, Qingdao (CN); Jiaqi Liu, Qingdao (CN); Keqiang He, Qingdao (CN); Likun Hua, Qingdao (CN)

(73) Assignee: Qingdao University of Technology (CN)

( * ) Notice: Subject to any disclaimer, the term of this patent is extended or adjusted under 35 U.S.C. 154(b) by 290 days.

(21) Appl. No.: 17/753,325

(22) PCT Filed: Oct. 29, 2021

(86) PCT No.: PCT/CN2021/127348
§ 371 (c)(1),
(2) Date: Feb. 28, 2022

(87) PCT Pub. No.: WO2022/142671
PCT Pub. Date: Jul. 7, 2022

(65) Prior Publication Data
US 2023/0033460 A1 Feb. 2, 2023

(30) Foreign Application Priority Data
Jan. 4, 2021 (CN) ............ 202110002272.5

(51) Int. Cl.
*G01N 3/12* (2006.01)
*G01N 3/24* (2006.01)
*G01N 15/08* (2006.01)

(52) U.S. Cl.
CPC .......... *G01N 3/12* (2013.01); *G01N 3/24* (2013.01); *G01N 15/0826* (2013.01); *G01N 2203/0025* (2013.01)

(58) Field of Classification Search
CPC ........ G01N 3/12; G01N 3/24; G01N 15/0826; G01N 2203/0025; G01N 15/0806;
(Continued)

(56) References Cited

U.S. PATENT DOCUMENTS

2018/0335494 A1  11/2018  Hakimuddin

FOREIGN PATENT DOCUMENTS

| CN | 102252918 A | 11/2011 |
| CN | 106092772 | * 11/2016 |

(Continued)

*Primary Examiner* — Robert R Raevis
(74) *Attorney, Agent, or Firm* — Brian M. Kaufman; Robert D. Atkins; PATENT LAW GROUP: Atkins and Associates, P.C.

(57) ABSTRACT

An integrated triaxial shear and seepage experimental method for hydrate-bearing sediments and device thereof is provided, relating to the field of geotechnical experiments technologies. The method includes the following steps: generating hydrate; preparing a shear and seepage coupling experiment; and performing the shear and seepage coupling experiment. According to a special integrated experimental device, that coupling analysis of seepage and stress in a triaxial shear breakage process of the hydrate can be realized, and different experiments that are liquid seepage experiment and the gas-liquid seepage experiment can be realized.

9 Claims, 5 Drawing Sheets

(58) Field of Classification Search
CPC ......... G01N 2203/0256; G01N 33/241; G01N 3/02; G01N 13/04
USPC .................................................. 73/866, 38
See application file for complete search history.

(56) References Cited

FOREIGN PATENT DOCUMENTS

| | | | |
|---|---|---|---|
| CN | 206192785 U | | 5/2017 |
| CN | 107121359 A | | 9/2017 |
| CN | 107894383 | * | 4/2018 |
| CN | 208076303 U | | 11/2018 |
| CN | 20200340895 | * | 10/2020 |
| CN | 111982782 A | * | 11/2020 ......... G01N 15/0826 |

* cited by examiner

INTEGRATED TRIAXIAL SHEAR AND SEEPAGE EXPERIMENTAL METHOD FOR HYDRATE-BEARING SEDIMENTS AND DEVICE THEREOF

CROSS REFERENCE TO RELATED APPLICATIONS

The present patent application is a national stage application of International Patent Application No. PCT/CN2021/127348, filed Oct. 29, 2021, which claims the benefit and priority to Chinese Patent Application No. 202110002272.5, entitled "integrated triaxial shear and seepage experimental method for hydrate-bearing sediments" filed with the Chinese Patent Office on Jan. 4, 2021, the disclosure of which is incorporated by reference herein in its entirety as part of the present application.

TECHNICAL FIELD

The present disclosure relates to the field of geotechnical experiment technologies, and in particular, to an integrated triaxial shear and seepage experimental method for hydrate-bearing sediment and a device thereof.

BACKGROUND ART

As a novel energy source, natural gas hydrate is widely distributed in various oceanic and terrestrial tundra regions in the world. The natural gas hydrate is widely considered as an alternative energy source in the twenty-first century due to its advantages of large reserves, wide distribution, and non-pollution, and the like. However, during the exploitation of hydrate, the decomposition of the hydrate will produce a large amount of gas, the cementation of the hydrate will disappear and thus excess pore pressure is produced. So, the change of mechanical characteristics and the reduction of strength of the hydrate-bearing sediments are caused. Further, a series of large-scale geological disasters will be eventually induced. Permeability, as an inherent attribute of the hydrate-bearing sediments, is an important basis for quality evaluation of natural gas hydrate reservoir, performance prediction of gas production, and formulation of exploitation solution. Therefore, the research on the mechanical characteristics and permeability characteristics of natural gas hydrate sediments is the premise to realize safe and efficient exploitation of the hydrate.

Because an in-situ drilling and coring manner is limited by severe storage conditions (i.e., at high pressure and low temperature) of the natural gas hydrate, the in-situ drilling and coring manner is not economical and practical. So, an indoor synthesizing manner is widely used in the research of the hydrate-bearing sediments. Firstly, the natural gas hydrate is generated in a high-pressure and low-temperature environment created artificially, and then specific research work of the mechanical characteristics, seepage characteristics, and the like are carried out.

The effective stress, the hydrate saturation, the pore pressure, and the like of the reservoir are dynamic, rather than constant, during the exploitation of the hydrate, so the seepage under the influence of a plurality of factors is also a dynamic process. At the same time, the effective stress that is applied to the reservoir will also change under the influence of the factors, such as the permeability and the saturation. Therefore, there is a two-field coupling and interaction process between the stress and the seepage.

Although there are a lot of mechanical equipment and seepage equipment for geotechnical experiments, the equipment, which is specially used for the hydrate-bearing sediments and can reflect the interaction of the stress and the seepage, is rare. Particularly, gas and liquid seepage experiments cannot be carried out during a triaxial shear process, i.e., a breakage process, of a sample, which brings great limitations to the integrated triaxial shear and seepage experiment for the hydrate-bearing sediments.

SUMMARY

An objective of the present disclosure is to provide an integrated triaxial shear and seepage experimental method for hydrate-bearing sediments and a device thereof. By using a special integrated experimental device, that coupling analysis of seepage and stress in a triaxial shear breakage process of the hydrate can be realized, and different experiments that are liquid seepage experiment and the gas-liquid seepage experiment can be realized.

The technical solution of the present disclosure is as follows:

An integrated triaxial shear and seepage experimental method for the hydrate-bearing sediments includes the following steps:

generating hydrate: generating the hydrate in a low-temperature and high-pressure environment by loading a sample, applying a confining pressure to the sample, applying a pore pressure to the sample, and cooling to the sample;

preparing a shear and seepage coupling experiment: setting corresponding different stage states of an axial pressure controller, a confining pressure controller, a pore pressure controller, a liquid seepage pressure controller, or a nitrogen seepage pressure controller in a preset stress path, and setting a pressure of a back pressure valve to be higher than a hydrate phase equilibrium pressure of a constant temperature gas bath at a preset temperature; and performing the shear and seepage coupling experiment: starting a device to perform the shear and seepage coupling experiment, and recording to data of both a sample base pressure sensor and a sample cap pressure sensor to serve as data of pressure difference data in a seepage experiment.

In some embodiments, the performing the shear and seepage coupling experiment may include: performing the shear and seepage coupling experiment after the pressure difference may be stable, or performing calculation in a manner of taking an average value in not less than three experiments when the pressure difference may be difficult to maintain stability.

In some embodiments, the loading the sample in may include: loading the sample according to a sequence of a sample base, a lower porous stone, the sample, an upper porous stone, and a sample cap from bottom to top, and tightening by using an upper rubber stirrup and a lower rubber stirrup; adjusting heights of a transverse beam of a triaxial instrument and a dowel bar, such that a lower end of the dowel bar and the sample cap may be in a critical state that the lower end and the sample cap are in contact with each other; creating a negative pressure environment inside the sample by using the pore pressure controller when the sample is a loose matrix sample, such that the sample may be in a vertical state.

In some embodiments, the applying the confining pressure to the sample may include: injecting hydraulic oil into a triaxial pressure chamber to apply a predetermined confining pressure by the confining pressure controller; applying the pore pressure to the sample may include: introducing methane gas into the sample through the pore pressure controller, where the pore pressure may be less than the confining pressure all the time; and cooling to the sample may include: decreasing a temperature to an experimental temperature by using the constant temperature gas bath.

An integrated triaxial shear and seepage experimental device for the hydrate-bearing sediments, the experimental device performing the integrated triaxial shear and seepage experimental method for the hydrate-bearing sediments, and includes a triaxial pressure chamber. An outer cover of a triaxial pressure chamber is arranged outside the triaxial pressure chamber, and is fixed to a sample base through nuts and a bolts of an outer cover of a triaxial instrument. A circle of through pores are formed in the sample base. The through pores include sample base seepage pores and sample base gas inlet pores formed alternately. The sample base seepage pores are connected with a seepage inlet pipe. The sample base gas inlet pores are connected with a pore pressure gas inlet pipe. The sample base is communicated with a sample through the sample base seepage pores and the sample base gas inlet pores. A seepage inlet pressure sensor is arranged on the seepage inlet pipe, and is used for monitoring a seepage inlet pressure. A first groove is formed in the sample base. A sample base pressure sensor is mounted in the first groove. A dowel bar is connected to a top of the outer cover of a triaxial pressure chamber through a dowel bar upper nut and a dowel bar lower nut. The height of the dowel bar may be adjusted through the dowel bar upper nut and the dowel bar lower nut. A top of the dowel bar is a concave hemisphere, and is matched with a convex hemisphere of a bottom of an upper ejector rod above top of the dowel bar. A lower part of the dowel bar is a convex hemisphere and is matched with a concave hemisphere of a top of the sample cap below the lower part of the dowel bar. A bottom of the triaxial pressure chamber is the sample base. A latex film is arranged above a center of the sample base. A center of the latex film wraps the sample. An upper end of the latex film is sleeved on the sample cap through an upper rubber stirrup, and the latex film is tightly attached with the sample cap. A lower end of the latex film is sleeved on the sample base through a lower rubber stirrup, and the latex film is tightly attached with the sample base. A circle of sample cap seepage pores are formed in the sample cap and are connected to a seepage outlet pipe. The seepage outlet pipe is communicated with the sample through the sample base and the sample cap. A seepage outlet pressure sensor is arranged on the seepage outlet pipe, and is used for monitoring a seepage outlet pressure. A second groove is formed in the sample cap. The sample cap pressure sensor is mounted in the second groove. A plurality of inlets and outlets of a seepage system are arranged uniformly, which can ensure stable pressure difference and uniform pressure difference distribution in a seepage experiment process. Meanwhile, the permeability of the sample is good. This is very important for some hydrate-bearing sediments with low permeability (such as argillaceous silty hydrate).

A methane gas cylinder is connected with a methane gas storage tank through a methane pressure adjustment valve, and the methane gas storage tank is connected with the sample base gas inlet pores through the pore pressure controller and a first pipeline, so as to provide methane gas required for synthesizing the hydrate. A nitrogen gas cylinder is connected with a nitrogen gas storage tank through a nitrogen pressure adjustment valve, and the nitrogen gas storage tank is connected with the sample base seepage pores through a nitrogen seepage pressure controller and a second pipeline, so as to provide gas required for seepage to the nitrogen seepage pressure controller. The methane gas storage tank and the nitrogen gas storage tank achieve a transition effect, and reduce gas pressure and temperature.

The gas storage tank is connected with the sample cap seepage pores through a gas-liquid separator and a third pipeline to store nitrogen produced by a seepage experiment. A water storage tank is connected with the sample cap seepage pores through the gas-liquid separator, which stores water produced by the seepage experiment, and a balance acquires quality of the water generated during seepage in real time. A gas flowmeter is arranged between the gas-liquid separator and the gas storage tank to monitor the volume of gas produced during the seepage.

An oil tank is connected with the confining pressure controller, so as to provide hydraulic oil for the confining pressure controller. The confining pressure controller is connected with the triaxial pressure chamber through a confining pressure liquid inlet pipe. The confining pressure liquid inlet pipe is communicated with the triaxial pressure chamber through the sample base. The water tank is connected with the liquid seepage pressure controller, so as to provide the liquid seepage pressure controller with a liquid required for the seepage. Here, water is adopted to perform the seepage experiment, and the liquid seepage pressure controller is connected to the sample base seepage pores through a fourth pipeline.

A vertical beam of a triaxial instrument is arranged outside the triaxial pressure chamber. A bottom of the vertical beam of a triaxial instrument is welded with a base of a triaxial instrument. An upper part of the vertical beam of a triaxial instrument is provided with screw threads, and is connected with a transverse beam of the triaxial instrument through upper nuts and lower nuts of the transverse beam. A height of the transverse beam of triaxial instrument may be adjusted through the transverse beam upper nut and a transverse beam lower nut. The axial pressure controller is arranged in a center of the base of a triaxial instrument, and is connected with the sample base through a telescopic shaft. An upper ejector rod is arranged at a middle part of the transverse beam of the triaxial instrument.

Valves are arranged on the first pipeline, the second pipeline, the third pipeline and the fourth pipeline respectively.

In some embodiments, each of the sample base seepage pores and an adjacent, corresponding one of the sample base gas inlet pores may be formed at an angle of 45 degrees. Adjacent two of the sample cap seepage pores may be formed at an angle of 90 degrees. In order to ensure stable pressure difference, uniform pressure difference distribution, and good permeability during the seepage, the sample base seepage pores, the sample base gas inlet pores, and the sample cap seepage pores may be all provided with multiple and distributed uniformly in the present disclosure. A central angle formed between each of the sample base gas inlet pore and adjacent, corresponding one of the sample base seepage pore may be 45 degrees, and a central angle formed between adjacent two the sample cap seepage pores may be 90 degrees.

In some embodiments, a first valve may be arranged between the methane pressure adjustment valve and the methane gas storage tank. A twelfth valve may be arranged between the nitrogen pressure adjustment valve and the nitrogen gas storage tank. A second valve may be arranged between the methane gas storage tank and the pore pressure controller. A third valve may be arranged between the pore pressure controller and the sample base gas inlet pores. A fourth valve may be arranged on the confining pressure liquid inlet pipe. A fifth valve may be arranged between the oil tank and the confining pressure controller. A sixth valve may be arranged on a main pipeline after the forth pipeline between the liquid seepage pressure controller and the sample base seepage pores and the second pipeline between the nitrogen seepage pressure controller and the sample base seepage pores may be converged. A ninth valve may be arranged on a first branch pipeline between the liquid seepage pressure controller and the sample base seepage pores, and an eighth valve may be arranged on a second branch pipeline between the nitrogen seepage pressure controller and the sample base seepage pores. A tenth valve may be arranged between the nitrogen seepage pressure controller and the nitrogen gas storage tank. An eleventh valve may be arranged between the water tank and the liquid seepage pressure controller. The back pressure valve may be arranged between the gas-liquid separator and the seepage outlet pressure sensor, so as to realize pressure control at the seepage outlet. A seventh valve may be arranged between the seepage outlet pressure sensor and the back pressure valve. The first valve, the second valve, the third valve, the fourth valve, the fifth valve, the sixth valve, the seventh valve, the eighth valve, the ninth valve, the tenth valve, the eleventh valve, and the twelfth valve may realize opening and closing of corresponding a pipeline.

In some embodiments, a pressure chamber pressure sensor and a pressure chamber temperature sensor may be arranged on the sample base. An axial force sensor may be arranged on the upper ejector rod.

In some embodiments, the pore pressure controller, the nitrogen seepage pressure controller, the confining pressure controller, the liquid seepage pressure controller, the balance, the gas flowmeter, the axial pressure controller, the telescopic shaft, the seepage outlet pressure sensor, the seepage inlet pressure sensor, the pressure chamber pressure sensor, the pressure chamber temperature sensor, the axial force sensor, the sample base pressure sensor, and the sample cap pressure sensor may be connected with a computer, which may realize real-time recording of related data. Each of the pore pressure controller, the nitrogen seepage pressure controller, the confining pressure controller, and the liquid seepage pressure controller includes a servo motor and a chamber with a certain volume, and may be subjected to pressure control through the computer. The axial pressure controller may include a servo motor, which may control length of the telescopic shaft. The change of the length of the telescopic shaft may reflect the displacement change of the sample during shear, and may be recorded by the computer in real time.

In some embodiments, except for the methane gas cylinder, the nitrogen gas cylinder, the methane pressure adjustment valve, the nitrogen pressure adjustment valve, the gas-liquid separator, the water storage tank, the balance, the gas flowmeter, the gas storage tank, and the computer, the sample base gas inlet pores, the seepage inlet pressure sensor, the dowel bar, the upper nut of the dowel bar, the lower nut of the dowel bar, the outer cover of the triaxial pressure chamber, the sample cap seepage pores, the seepage outlet pressure sensor, the methane gas storage tank, the oil tank, the triaxial pressure chamber, the vertical beam of the triaxial instrument, the upper nuts of the transverse beam, the lower nuts the transverse beam, the transverse beam of the triaxial instrument, the base of the triaxial instrument, the axial pressure controller, the upper ejector rod, the pore pressure controller, the confining pressure controller, the nitrogen seepage pressure controller, the nitrogen gas storage tank, the water tank, the liquid seepage pressure controller, the sample base may be in the constant temperature gas bath.

Compared with the prior art, the embodiment has the following advantages.

(1) Based on the conventional pseudo-triaxial experimental system, a seepage experiment is added to realize "shear and seepage" coupling analysis based on a pseudo triaxial stress condition. Meanwhile, a separate shear experiment or a seepage experiment in a specific triaxial state can be performed. When the separate shear experiment is performed, it is only necessary to close the valves for the seepage system. When the seepage experiment in the specific triaxial state is performed, it is only necessary to keep the axial pressure, the confining pressure, and the pore pressure constant. Meanwhile, the present disclosure can also perform the seepage experiment in a triaxial shear process, i.e., a breakage process, of the sample.

(2) On the basis of realizing the "shear and seepage" coupling analysis, in-situ hydrate synthesis equipment is added, and the equipment may be used for researching in-situ synthesis of the hydrate-bearing sediments.

(3) A gas seepage way and a liquid seepage way are provided to solve the decoupling problem between single seepage and different scientific research purposes.

(4) The existing equipment generally uses the pressure data of both a seepage inlet pressure control device (such as the nitrogen seepage pressure controller or the liquid seepage pressure controller in the present disclosure) and a seepage outlet pressure control device (such as the back pressure valve in the present disclosure) to calculate the permeability. However, the actual pressure difference between the seepage inlet and the seepage outlet of the sample is usually not equal to the pressure difference between the seepage inlet pressure control device and the seepage outlet pressure control device, which will cause some errors in experimental data. According to the present disclosure, four dedicated pressure sensors are added to the seepage system, namely, the seepage outlet pressure sensor, the seepage inlet pressure sensor, the sample base pressure sensor, and the sample cap pressure sensor. The four dedicated pressure sensors respectively perform pressure monitoring on different positions in the seepage system. The data of the pressure from an interior of the sample is adopted, rather than the pressure data of both the seepage inlet pressure control device and the seepage outlet pressure control device. The seepage outlet pressure sensor acquires the pressure of the seepage outlet pipe. The seepage inlet pressure sensor acquires the pressure of the seepage inlet pipe. The sample base pressure sensor acquires the pressure of the lower end of the sample. The sample cap pressure sensor acquires the pressure of a top end of the sample. When the permeability is calculated by using Darcy's law in practice, the data of both the sample base pressure sensor and the sample cap pressure sensor are adopted, while the pressures of all of the back pressure valve, the nitrogen seepage pressure controller, the liquid seepage pressure controller is only used as reference, which is very different from the existing equipment. Meanwhile, the seepage outlet pressure sensor and the seepage inlet pressure sensor can realize the correction of the nitrogen seepage pressure controller, the liquid seepage pressure controller, and the back pressure valve, and can further acquire the error values of both the pressure difference of the sample and the pressure difference of the seepage control device, so that the data of pressure difference is more accurate.

(5) The existing equipment can rarely and separately perform seepage of two phases that are gas and liquid. Even if the seepage of two phases that are the gas and the liquid can be performed, the gas-liquid separation cannot be performed. However, no matter pure gas seepage or pure liquid seepage, or the gas-liquid two-phase seepage, due to the different design principles of gas metering equipment and liquid metering equipment, the statistical accuracy will be affected due to the existence of two phases that are the gas and the liquid, when flow statistics at the seepage outlet is performed. Even a larger error will be caused when the accuracy of both the gas metering equipment and liquid metering equipment is not enough. In addition, for the gas seepage, the existence of water is inevitable in the gas, which will affect the service life of gas storage equipment or gas metering equipment. A gas-liquid separator is added to the seepage system of the present disclosure, and the gas and the liquid are metered respectively, which reduces the metering errors of both the gas metering equipment and the liquid metering equipment, improves the calculation accuracy, and prolongs the service life of the equipment.

(6) The confining pressure, the axial pressure, the pore pressure, and the pressure of the seepage system are controlled by the computer, which overcomes the disadvantages in conventional manual control and realizes automatic collection of the data.

(7) For the synthesis of the hydrate-containing sediments and a permeability experiment thereof, the low-temperature pre-cooling needs to be performed on the triaxial pressure chamber and a seepage medium. While the existing equipment only performs low-temperature control on the triaxial pressure chamber. When pre-cooling equipment is increased, temperature control is realized in a water bath manner, which will result in that a chamber for storing the liquid must be provided. It is apparent that the manufacturing requirements of a chamber with a specific shape are also high. When constant temperature control needs to be performed on more equipment, a prefabricated chamber required for a water bath is difficult to be manufactured, and is high in costs. The present disclosure changes the water bath manner adopted by the existing equipment, and adopts a gas bath with wide applicability to perform temperature control, which achieves the purpose of a constant temperature of a plurality of sets of equipment without increasing additional costs.

(8) The seepage inlet and the seepage outlet of the seepage system adopt such a manner of uniformly arranging pores thereof, which can ensure the stable pressure difference and the uniform pressure difference distribution during the seepage experiment. Meanwhile, the permeability of the sample is good. This is very important for hydrate-bearing sediments with low permeability (such as argillaceous silty hydrate).

BRIEF DESCRIPTION OF THE DRAWINGS

The present disclosure will be further described below with reference to the accompanying drawings.

Figure 1:
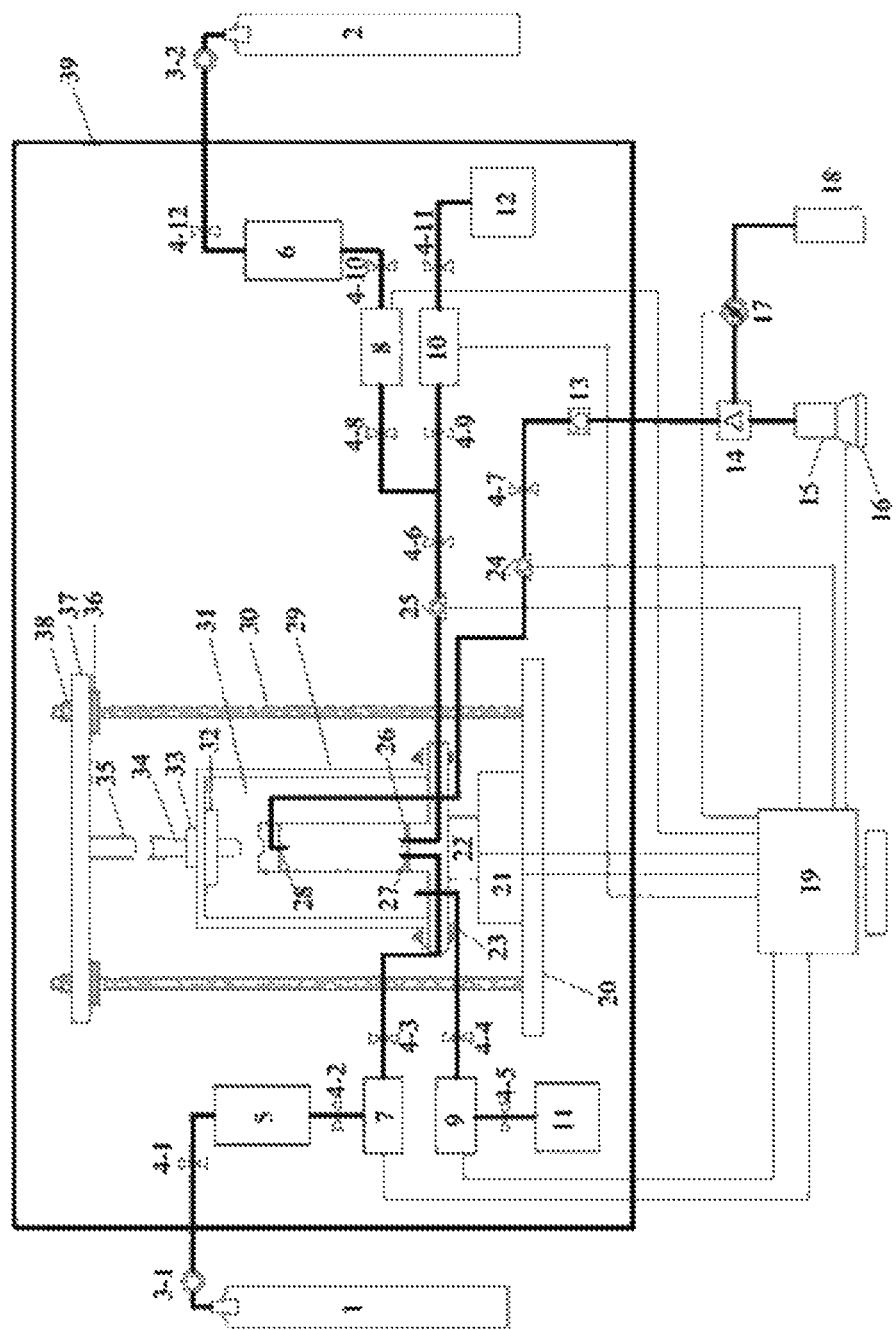
FIG. 1 is a schematic diagram showing an overall structure according to the present disclosure.

List of the reference characters: 1 methane gas cylinder; 2 nitrogen gas cylinder; 3-1 methane pressure adjustment valve, 3-2 nitrogen pressure adjustment valve; 5 methane gas storage tank; 6 nitrogen gas storage tank; 7 pore pressure controller; 8 nitrogen seepage pressure controller; 9 confining pressure controller; 10 liquid seepage pressure controller; 11 oil tank; 12 water tank; 13 back pressure valve; 14 gas-liquid separator; 15 water storage tank; 16 balance; 17 gas flowmeter; 18 gas storage tank; 19 computer; 20 base of a triaxial instrument; 21 axial pressure controller; 22 telescopic shaft; 23 sample base; 24 seepage outlet pressure sensor; 25 seepage inlet pressure sensor; 26 sample base seepage pore; 27 sample base gas inlet pore; 28 sample cap seepage pore; 29 outer cover of a triaxial pressure chamber; 30 vertical beam of a triaxial instrument; 31 triaxial pressure chamber; 32 dowel bar lower nut; 33 dowel bar upper nut; 34 dowel bar; 35 upper ejector rod; 36 transverse beam lower nut; 37 transverse beam of a triaxial instrument; 38 transverse beam upper nut; 39 constant temperature gas bath; 40 confining pressure liquid inlet pipe; 41 pore pressure gas inlet pipe; 42 pressure chamber pressure sensor; 43 pressure chamber temperature sensor; 44 lower porous stone; 45 upper porous stone; 46 sample cap; 47 seepage outlet pipe; 48 seepage inlet pipe; 49 nut of an outer cover of a triaxial instrument; 50 bolt of an outer cover of a triaxial instrument; 51 lower rubber stirrup; 52 sample; 53 latex film; 54 upper rubber stirrup; 55 axial force sensor; 56 sample base pressure sensor; and 57 sample cap pressure sensor.

DETAILED DESCRIPTION OF THE EMBODIMENTS

The technical solutions in the embodiments of the present disclosure will be described in detail below with reference to the drawings in the embodiments of the present disclosure. It is apparent that the described embodiments are merely a part of the embodiments of the present disclosure rather than all of the embodiments. Based on the embodiments of the present disclosure, all other embodiments obtained by those skilled in the art without creative work belong to the scope of protection of the present disclosure.

The purpose of the present disclosure is to provide an integrated triaxial shear and seepage experimental method and device for hydrate-bearing sediments. By using a special integrated experimental device, that coupling analysis of seepage and stress in a triaxial shear breakage process of hydrate can be realized, and different seepage experiments that are the liquid seepage experiment and the gas-liquid seepage experiment can be realized.

In order to make the above-mentioned purpose, features, and advantages of the present disclosure more apparent and more comprehensible, the present disclosure is further described in detail below with reference to the drawings and specific implementation manners.

Embodiment 1

Figure 2:
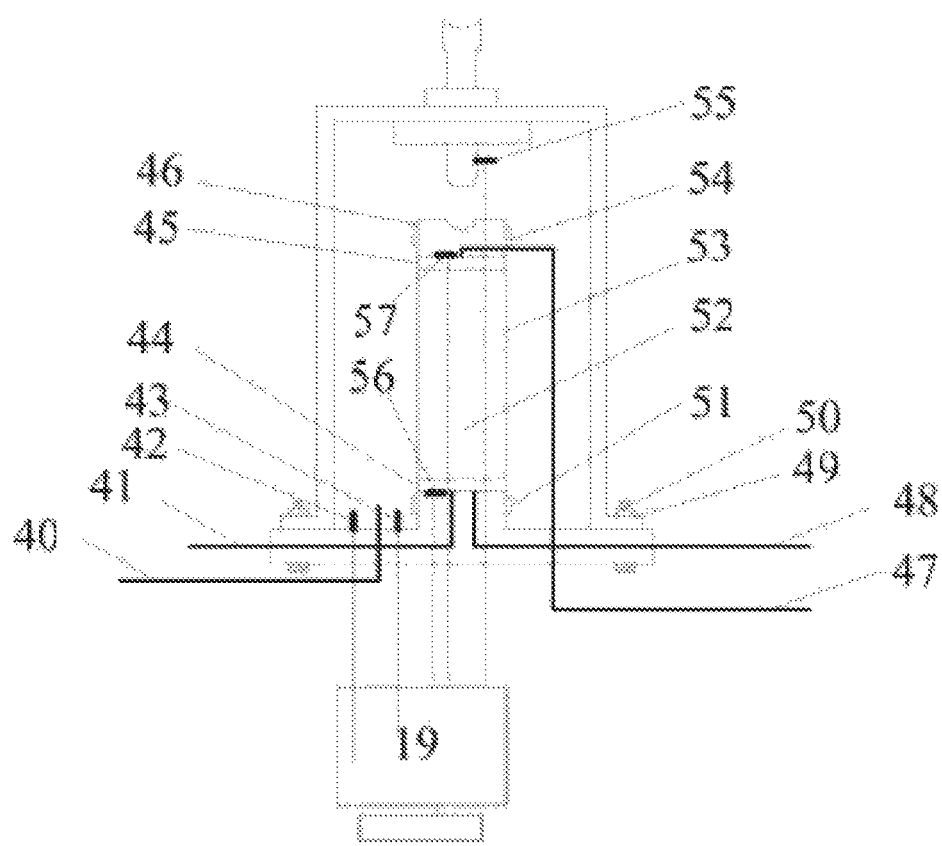
FIG. 2 is a schematic structural diagram of a pressure chamber according to the present disclosure.
Figure 3:
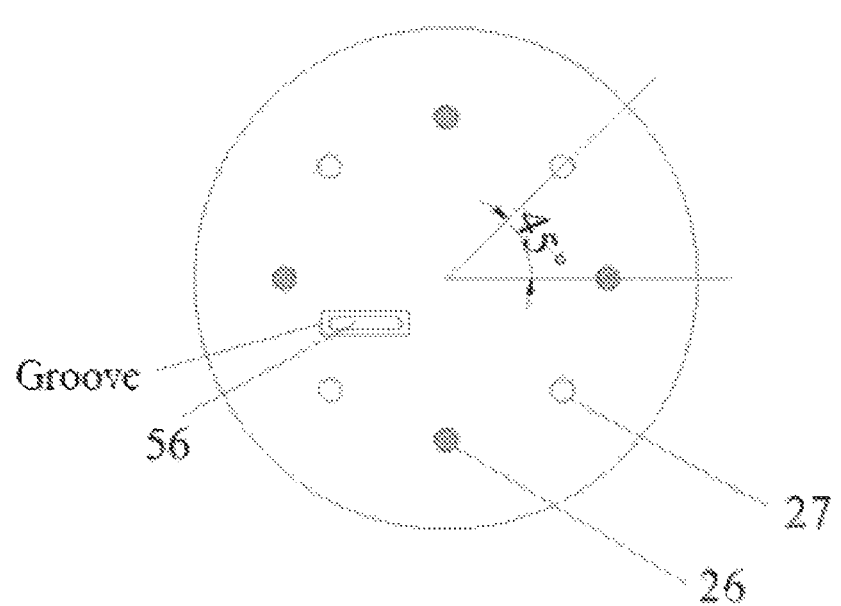
FIG. 3 is a schematic diagram of distribution of sample base seepage pores and sample base gas inlet pores.
Figure 4:
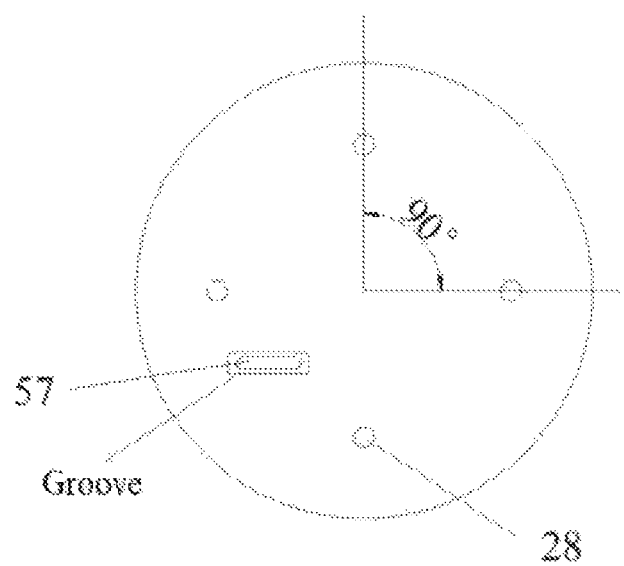
FIG. 4 is a schematic diagram of distribution of sample cap seepage pores.
Figure 5:
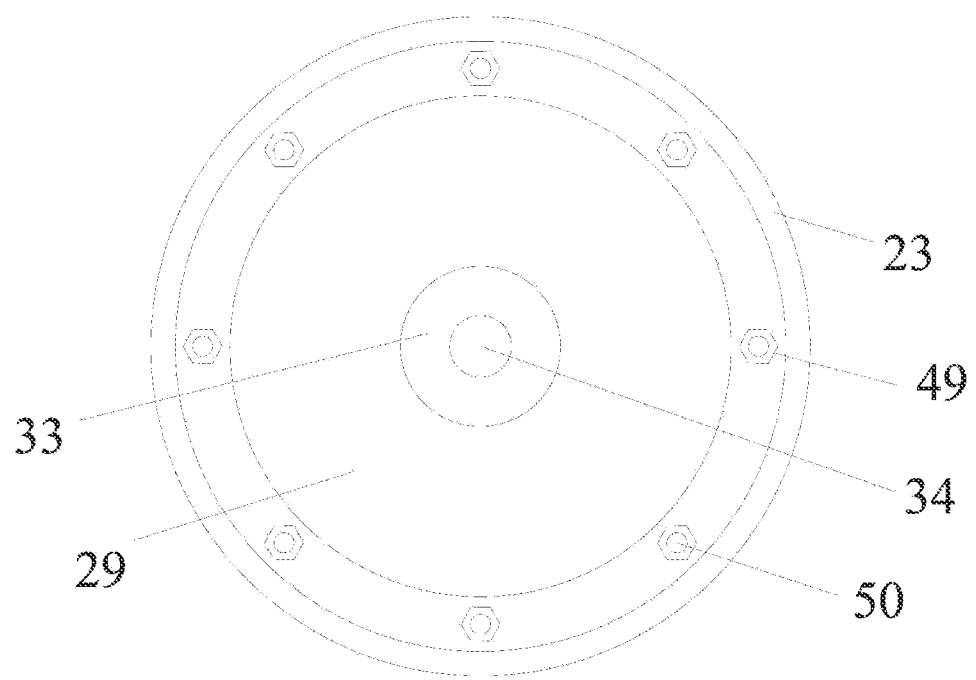
FIG. 5 is a top view of FIG. 2.

The integrated triaxial shear and seepage experimental device includes a triaxial pressure chamber 31, as shown in FIG. 2 and FIG. 5. An outer cover of a triaxial pressure chamber 29 is arranged outside the triaxial pressure chamber 31, and is fixed to a sample base 23 through nuts of an outer cover of a triaxial instrument 49 and bolts of the outer cover of the triaxial instrument 50. As shown in FIG. 3, a circle of through pores are formed in the sample base 23. The through pores include sample base seepage pores 26 and sample base gas inlet pores 27 formed alternately. The sample base seepage pores 26 are connected with a seepage inlet pipe 48. The sample base gas inlet pores 27 are connected with a pore pressure gas inlet pipe 41. The sample base 23 is communicated with a sample 52 through the sample base seepage pores and the sample base gas inlet pores. A seepage inlet pressure sensor 25 is arranged on the seepage inlet pipe 48, and is configured for monitoring pressure of a seepage inlet. A groove is formed in the sample base 23. A sample base pressure sensor 56 is mounted in the groove. A dowel bar 34 is connected to a top of the outer cover 29 through a dowel bar upper nut 33 and a dowel bar lower nut 32. The height of the dowel bar 34 can be adjusted through the dowel bar upper nut 33 and the dowel bar lower nut 32. A top of the dowel bar 34 is a concave hemisphere, and is matched with a convex hemisphere of a bottom of an upper ejector rod 35 above the dowel bar 34; and a lower part of the dowel bar 34 is a convex hemisphere and is matched with a concave hemisphere of a top of a sample cap 46 below the dowel bar. A bottom of the triaxial pressure chamber 31 is the sample base 23. A latex film 53 is arranged above a center of the sample base 23. A center of the latex film 53 wraps the sample 52. An upper end of the latex film 53 is sleeved on the sample cap 46 through the upper rubber stirrup 54, and the latex film 53 is tightly attached with the sample cap 46. A lower end of the latex film 53 is sleeved on the sample base 23 through the lower rubber stirrup 51, and the latex film 53 is tightly attached with the sample base 23. As shown in FIG. 4, a circle of sample cap seepage pores 28 are formed in the sample cap 46 and are connected to a seepage outlet pipe 47. The seepage outlet pipe 47 is communicated with the sample 52 through the sample base 23 and the sample cap 46. A seepage outlet pressure sensor 24 is arranged on the seepage outlet pipe 47, and is configured for monitoring pressure of a seepage outlet. A groove is formed in the sample cap 46. A sample cap pressure sensor 57 is mounted in the groove. The seepage inlet and the seepage outlet of a seepage system adopt such a manner of uniformly arranging pores thereof, which can ensure stable pressure difference and uniform pressure difference distribution during a seepage experiment. Meanwhile, the permeability of the sample is good. This is very important for hydrate-bearing sediments with low permeability (such as argillaceous silty hydrate).

A methane gas cylinder 1 is connected with a methane gas storage tank 5 through a methane pressure adjustment valve 3-1, and the methane gas storage tank 5 is connected with the sample base gas inlet pores 27 through the pore pressure controller 7 and a first pipeline, so as to provide methane gas required for synthesizing the hydrate. A nitrogen gas cylinder 2 is connected with a nitrogen gas storage tank 6 through a nitrogen pressure adjustment valve 3-2, and the nitrogen gas storage tank 6 is connected with sample base seepage pores 26 through a nitrogen seepage pressure controller 8 and a second pipeline, so as to provide the nitrogen seepage pressure controller 8 with the gas required for seepage. The methane gas storage tank 5 and the nitrogen gas storage tank 6 achieve a transition effect, and reduce the gas pressure and the temperature.

The gas storage tank 18 is connected with sample cap seepage pores 28 through a gas-liquid separator 14 and a third pipeline to store nitrogen produced by the seepage experiment. A water storage tank 15 is connected with the sample cap seepage pores 28 through the gas-liquid separator 14, which stores the water produced by the seepage experiment, and a balance 16 acquires the quality of the water generated during seepage experiment in real time. A gas flowmeter 17 is arranged between the gas-liquid separator 14 and the gas storage tank 18 to monitor the volume of gas produced by the seepage experiment.

An oil tank 11 is connected to a confining pressure controller 9, so as to provide hydraulic oil for the confining pressure controller 9. The confining pressure controller 9 is connected with the triaxial pressure chamber 31 through a confining pressure liquid inlet pipe 40. The confining pressure liquid inlet pipe 40 is communicated with the triaxial pressure chamber 31 through the sample base 23. The water tank 12 is connected with the liquid seepage pressure controller 10, so as to provide the liquid seepage pressure controller 10 with a liquid required for the seepage. Here, water is adopted to perform the seepage experiment, and the liquid seepage pressure controller 10 is connected with the sample base seepage pores 26 through a fourth pipeline.

As shown in FIG. 1, a vertical beam of a triaxial instrument 30 is arranged outside the triaxial pressure chamber 31. A bottom of the vertical beam 30 is welded with a base of a triaxial instrument 20. An upper part of the vertical beam 30 is provided with screw threads, and is connected with the transverse beam 37 through a transverse beam upper nut 38 and a transverse beam lower nut 36. The height of the transverse beam 37 can be adjusted through the transverse beam upper nut 38 and a transverse beam lower nut 36. An axial pressure controller 21 is arranged in a center of the base 20, and is connected with the sample base 23 through a telescopic shaft 22. An upper ejector rod 35 is arranged at a middle part of the transverse beam 37.

Valves are arranged on the first pipeline, the second pipeline, the third pipeline and the fourth pipeline respectively.

A pressure chamber pressure sensor 42 and a pressure chamber temperature sensor 43 are arranged on the sample base 23. An axial force sensor 55 is arranged on the upper ejector rod 35.

Except for the methane gas cylinder 1, the nitrogen gas cylinder 2, the methane pressure adjustment valve 3-1, the nitrogen pressure adjustment valve 3-2, the gas-liquid separator 14, the water storage tank 15, the balance 16, the gas flowmeter 17, the gas storage tank 18, and the computer 19, the sample base gas inlet pores, the seepage inlet pressure sensor, the dowel bar, the upper nut of the dowel bar, the lower nut of the dowel bar, the outer cover of the triaxial pressure chamber, the sample cap seepage pores, the seepage outlet pressure sensor, the methane gas storage tank, the oil tank, the triaxial pressure chamber, the vertical beam of the triaxial instrument, the upper nuts of the transverse beam, the lower nuts the transverse beam, the transverse beam of the triaxial instrument, the base of the triaxial instrument, the axial pressure controller, the upper ejector rod, the pore pressure controller, the confining pressure controller, the nitrogen seepage pressure controller, the nitrogen gas storage tank, the water tank, the liquid seepage pressure controller, the sample base are in a constant temperature gas bath 39.

The integrated triaxial shear and seepage experimental method is realized through the integrated triaxial shear and seepage experimental device.

By using the above-mentioned integrated triaxial shear and seepage experimental device for the hydrate-bearing sediments, the experimental method of the present disclosure mainly includes the following steps 1 to 7.

In step 1, a sample is loaded. The sample is loaded according to a sequence of the sample base 23, a lower porous stone 44, the sample 52, an upper porous stone 45, and the sample cap 46 from bottom to top, and the sample is tightened by using an upper rubber stirrup 54 and a lower rubber stirrup 51. The heights of the transverse beam 37 of a triaxial instrument and the dowel bar 34, so that a lower end of the dowel bar 34 and the sample cap 46 are in a critical state that the lower end and the sample cap are in contact with each other. It is to be noted that a vertical sample is difficult to form for some loosen matrix samples, such as coarse sandy soil due to poor independence of the sample 52. For this problem, the present method creates a negative pressure environment inside the sample 52 by using the pore pressure controller 7. At this time, the sample 52 may be in a vertical state under an ambient atmospheric pressure.

In step 2, confining pressure to the sample is applied. After the sample is filled and the triaxial pressure outer cover 29 is connected with the sample base 23 by using the nuts 49 and the bolts 50, the hydraulic oil is injected into the triaxial pressure chamber 31 by using the confining pressure controller 9, so as to apply a certain confining pressure to the sample.

In step 3, pore pressure is applied. The methane gas is introduced into the sample 52 through the pore pressure controller 7, the pore pressure is less than the confining pressure all the time. At this time, a seventh valve 4-7 on the seepage outlet pipe 47 and a sixth valve 4-6 on the seepage inlet pipe 48 are kept closed.

In step 4, cooling is performed. The temperature is decreased to experimental temperature by using the constant temperature gas bath 39.

In step 5, hydrate is generated. The confining pressure is adjusted through the confining pressure controller 9, the pore pressure is adjusted through the pore pressure controller 7, and the hydrate is generated in a low-temperature and high-pressure environment. The pore pressure should be higher than the hydrate phase equilibrium pressure of the constant temperature gas bath 39 at a set temperature. The synthesis process generally lasts for over 24 hours.

In step 6, the shear and seepage coupling experiment is prepared. According to a research purpose, corresponding states of the axial pressure controller 21, the confining pressure controller 9, the pore pressure controller 7, the liquid seepage pressure controller 10 (liquid seepage), or the nitrogen seepage pressure controller 8 (gas seepage) under a preset stress path at different stages are set by using a computer 19. The pressure of a back pressure valve 13 is set, and the pressure of the back pressure value should be higher than the hydrate phase equilibrium pressure of the constant temperature gas bath 39 at a set temperature.

In step 7, the experiment is started. Firstly, a third valve 4-3 on the pore pressure gas inlet pipe 41 is closed. Then, the computer 19 starts the liquid seepage pressure controller 10 (liquid seepage) or the nitrogen seepage pressure controller 8 (gas seepage). Next, a seventh valve 4-7 on the seepage outlet pipe 47 and a sixth valve 4-6 on the seepage inlet pipe 48 are opened. Finally, the computer 19 starts the axial pressure controller 21, the confining controller 9, and the pore pressure controller 7 to perform a shear experiment. It is to be noted that when experimental data is processed, the data of pressure difference of the seepage experiment must adopt the data of the sample base pressure sensor 56 and the sample cap pressure sensor 57, rather than adopting the data of the back pressure valve 13, the nitrogen seepage pressure controller 8, and the liquid seepage pressure controller 10.

Meanwhile, for the possible problem of pressure difference instability, the shear and seepage coupling experiment is carried out after the pressure difference is stable. If stable pressure difference is difficult to keep, a method of taking an average value of three experiments is adopted to further eliminate an error caused by the fluctuation of the pressure difference. The method of taking the average value should ensure that the numbers of experiments is not less than three times.

The above steps are only major steps. Some secondary steps, such as air tightness check, and opening and closing control of various valves are not elaborated herein. In addition, the above steps aim at a process of a shear and seepage coupling experiment, and it is apparent that the device can perform a separate triaxial shear or a separate seepage experiment according to research requirements. According to the present disclosure, triaxial shear, seepage, and shear and seepage coupling experiments considering the influence of the decomposition of the hydrate can also be performed by changing temperature-pressure conditions.

Embodiment 2

Each of the sample base seepage pores 26 and an adjacent, corresponding one of the sample base gas inlet pores 27 are formed at an angle of 45 degrees. Adjacent two of the sample cap seepage pores 28 are formed at an angle of 90 degrees. In order to ensure stable pressure difference, uniform pressure difference distribution, and good permeability during seepage, the sample base seepage pores 26, the sample base gas inlet pores 27, and the sample cap seepage pores 28 are multiple and distributed uniformly in the present disclosure, as shown in FIG. 3 and FIG. 4. A central angle formed between each of the sample base gas inlet pores and an adjacent, corresponding one of the sample base seepage pores is 45 degrees, as shown in FIG. 3; and a central angle formed between adjacent two of the sample cap seepage pores 28 is 90 degrees.

The rest part of embodiment 2 is the same as the corresponding part of Embodiment 1.

Embodiment 3

A first valve 4-1 is arranged between the methane pressure adjustment valve 3-1 and the methane gas storage tank 5. A twelfth valve 4-12 is arranged between the nitrogen pressure adjustment valve 3-2 and a nitrogen gas storage tank 6. A second valve 4-2 is arranged between the methane gas storage tank 5 and the pore pressure controller 7. A third valve 4-3 is arranged between the pore pressure controller 7 and the sample base gas inlet pores 27. A fourth valve 4-4 is arranged on the confining pressure liquid inlet pipe 40. A fifth valve 4-5 is arranged between the oil tank 11 and the confining pressure controller 9. A sixth valve 4-6 is arranged on a main pipeline after the forth pipeline between the liquid seepage pressure controller 10 and the sample base seepage pores 26 and the second pipeline between the nitrogen seepage pressure controller 8 and the sample base seepage pores 26 are converged. A ninth valve 4-9 is arranged on a first branch pipeline between the liquid seepage pressure controller 10 and the sample base seepage pores 26, and an eighth valve 4-8 is arranged on a second branch pipeline between the nitrogen seepage pressure controller 8 and the sample base seepage pores 26. A tenth valve 4-10 is arranged between the nitrogen seepage pressure controller 8 and the nitrogen gas storage tank 6. An eleventh valve 4-11 is arranged between the water tank 12 and the liquid seepage pressure controller 10. The back pressure valve 13 is arranged between the gas-liquid separator 14 and a seepage outlet pressure sensor 24, so as to realize control of pressure at the seepage outlet. A seventh valve 4-7 is arranged between the seepage outlet pressure sensor 24 and the back pressure valve 13. The first valve 4-1, the second valve 4-2, the third valve 4-3, the fourth valve 4-4, the fifth valve 4-5, the sixth valve 4-6, the seventh valve 4-7, the eighth valve 4-8, the ninth valve 4-9, the tenth valve 4-10, the eleventh valve 4-11, and the twelfth valve 4-12 realize the opening and closing of various pipelines.

The rest part of embodiment 3 is the same as the corresponding part of Embodiment 1.

Embodiment 4

The pore pressure controller 7, the nitrogen seepage pressure controller 8, the confining pressure controller 9, the liquid seepage pressure controller 10, the balance 16, the flowmeter 17, the axial pressure controller 21, the telescopic shaft 22, the seepage outlet pressure sensor 24, the seepage inlet pressure sensor 25, the pressure chamber pressure sensor 42, the pressure chamber temperature sensor 43, the axial force sensor 55, the sample base pressure sensor 56, and the sample cap pressure sensor 57 are connected with the computer 19, which can realize real-time recording of related data. Each of the pore pressure controller 7, the nitrogen seepage pressure controller 8, the confining pressure controller 9, and the liquid seepage pressure controller 10 includes a first servo motor and a chamber with a certain volume, and can be subjected to pressure control through the computer 19. The axial pressure controller 21 includes a second servo motor, which can control the length of the telescopic shaft 22. The change of the length of the telescopic shaft 22 reflects the displacement change of the sample 52 during shear, and is recorded by the computer 19 in real time.

The rest part of embodiment 3 is the same as the corresponding part of Embodiment 1.

The implementation manner of the present disclosure is described in detail in combination with the accompanying drawings above, but the present disclosure is not limited to the above implementation manner. Within the scope of knowledge possessed by those of ordinary skill in the art, various changes can be made without departing from the purpose of the present disclosure.

What is claimed is:
1. An integrated triaxial shear and seepage experimental method for hydrate-bearing sediments, the experimental method comprising:
a step of generating a hydrate in a low-temperature and high-pressure environment comprising,
loading a sample base,
loading a lower porous stone over the sample base,
loading a sample over the lower porous stone,
loading an upper porous stone over the sample,
loading a sample cap over the upper porous stone,
tightening by using an upper rubber stirrup and a lower rubber stirrup,
adjusting heights of a transverse beam of a triaxial instrument and a dowel bar, such that a lower end of the dowel bar and the sample cap are in a critical state that the lower end and the sample cap are in contact with each other,
creating a negative pressure environment inside the sample by using the pore pressure controller when the sample is a loose matrix sample, such that the sample is in a vertical state,
applying a confining pressure to the sample,
applying a pore pressure to the sample, and
cooling the sample;
a step of preparing a shear and seepage coupling experiment comprising,
setting corresponding different stage states of one of an axial pressure controller, a confining pressure controller, a pore pressure controller, a liquid seepage pressure controller, and a nitrogen seepage pressure controller in a preset stress path, and
setting a pressure of a back pressure valve to be higher than a hydrate phase equilibrium pressure of a constant temperature gas bath at a preset temperature; and
a step of performing the shear and seepage coupling experiment comprising,
starting a device to perform the shear and seepage coupling experiment, and
recording both a sample base pressure sensor and a sample cap pressure sensor to serve as data of pressure difference in the shear and seepage coupling experiment.

2. The integrated triaxial shear and seepage experimental method for hydrate-bearing sediments according to claim 1, wherein applying the confining pressure to the sample comprises: injecting hydraulic oil into a triaxial pressure chamber to apply a predetermined confining pressure by the confining pressure controller; applying the pore pressure to the sample comprises: introducing methane gas into the sample through the pore pressure controller, wherein the pore pressure is less than the confining pressure; and cooling to the sample comprises: decreasing a temperature of the sample to an experimental temperature by using the constant temperature gas bath.

3. The integrated triaxial shear and seepage experimental method for hydrate-bearing sediments according to claim 1, wherein the step of performing the shear and seepage coupling experiment is performed in a manner of taking an average value of not less than three experiments.

4. An integrated triaxial shear and seepage experimental device for hydrate-bearing sediments, the according to claim 1, the experimental device comprising:
a triaxial pressure chamber, wherein an outer cover of the triaxial pressure chamber is arranged outside the triaxial pressure chamber, and is fixed to a sample base through nuts and bolts of an outer cover of a triaxial instrument; a circle of through pores are formed in the sample base; the through pores comprise sample base seepage pores and sample base gas inlet pores formed alternately; the sample base seepage pores are connected with a seepage inlet pipe; the sample base gas inlet pores are connected with a pore pressure gas inlet pipe; a seepage inlet pressure sensor is arranged on the seepage inlet pipe; a first groove is formed in the sample base; a sample base pressure sensor is mounted in the first groove; a dowel bar is connected to a top of the outer cover of the triaxial pressure chamber through an upper nut and a lower nut of the dowel bar; a top of the dowel bar is a concave hemisphere, and is matched with a convex hemisphere of a bottom of an upper ejector rod above the top of the dowel bar; a lower part of the dowel bar is a convex hemisphere and is matched with a concave hemisphere of a top of a sample cap below the lower part of the dowel bar; a bottom of the triaxial pressure chamber is the sample base; a latex film is arranged above a center of the sample base; a center of the latex film wraps a sample; an upper end of the latex film is sleeved on the sample cap through an upper rubber stirrup, and a lower end of the latex film is sleeved on the sample base through a lower rubber stirrup; a circle of sample cap seepage pores are formed in the sample cap and are connected to a seepage outlet pipe; a seepage outlet pressure sensor is arranged on the seepage outlet pipe; a second groove is formed in the sample cap; a sample cap pressure sensor is mounted in the second groove;

a methane gas cylinder is connected with a methane gas storage tank through a methane pressure adjustment valve, and the methane gas storage tank is connected with the sample base gas inlet pores through a pore pressure controller and a first pipeline; a nitrogen gas cylinder is connected with a nitrogen gas storage tank through a nitrogen pressure adjustment valve, and the nitrogen gas storage tank is connected with the sample base seepage pores through a nitrogen seepage pressure controller and a second pipeline;

a gas storage tank is connected with the sample cap seepage pores through a gas-liquid separator and a third pipeline; a water storage tank is connected with the sample cap seepage pores through the gas-liquid separator, and a balance acquires quality of water generated during seepage in real time; a gas flowmeter is arranged between the gas-liquid separator and the gas storage tank;

an oil tank is connected with a confining pressure controller; the confining pressure controller is connected with the triaxial pressure chamber through a confining pressure liquid inlet pipe; the confining pressure liquid inlet pipe is communicated with the triaxial pressure chamber through the sample base; a water tank is connected with a liquid seepage pressure controller; the liquid seepage pressure controller is connected with the sample base seepage pores through a fourth pipeline;

a vertical beam of the triaxial instrument is arranged outside the triaxial pressure chamber; a bottom of the vertical beam of the triaxial instrument is welded with a base of the triaxial instrument; an upper part of the vertical beam of the triaxial instrument is provided with screw threads, and is connected with a transverse beam of the triaxial instrument through upper nuts and lower nuts of the transverse beam;

an axial pressure controller is arranged in a center of the base of the triaxial instrument, and is connected with the sample base through a telescopic shaft; an upper ejector rod is arranged at a middle part of the transverse beam of the triaxial instrument; and valves are arranged on the first pipeline, the second pipeline, the third pipeline and the fourth pipeline respectively.

5. The integrated triaxial shear and seepage experimental device for hydrate-bearing sediments according to claim 4, wherein each of the sample base seepage pores and an adjacent, corresponding one of the sample base gas inlet pores are formed at an angle of 45 degrees; and adjacent two of the sample cap seepage pores are formed at an angle of 90 degrees.

6. The integrated triaxial shear and seepage experimental device for hydrate-bearing sediments according to claim 4, wherein a first valve is arranged between the methane pressure adjustment valve and the methane gas storage tank; a twelfth valve is arranged between the nitrogen pressure adjustment valve and the nitrogen gas storage tank; a second valve is arranged between the methane gas storage tank and the pore pressure controller; a third valve is arranged between the pore pressure controller and the sample base gas inlet pores; a fourth valve is arranged on the confining pressure liquid inlet pipe; a fifth valve is arranged between the oil tank and the confining pressure controller; a sixth valve is arranged on a main pipeline after the forth pipeline between the liquid seepage pressure controller and the sample base seepage pores and the second pipeline between the nitrogen seepage pressure controller and the sample base seepage pores are converged; a ninth valve is arranged on a first branch pipeline between the liquid seepage pressure controller and the sample base seepage pores, and an eighth valve is arranged on a second branch pipeline between the nitrogen seepage pressure controller and the sample base seepage pores; a tenth valve is arranged between the nitrogen seepage pressure controller and the nitrogen gas storage tank; an eleventh valve is arranged between the water tank and the liquid seepage pressure controller; a back pressure valve is arranged between the gas-liquid separator and the seepage outlet pressure sensor; and a seventh valve is arranged between the seepage outlet pressure sensor and the back pressure valve.

7. The integrated triaxial shear and seepage experimental device for hydrate-bearing sediments according to claim 4, wherein a pressure chamber pressure sensor and a pressure chamber temperature sensor are arranged on the sample base; and an axial force sensor is arranged on the upper ejector rod.

8. The integrated triaxial shear and seepage experimental device for hydrate-bearing sediments according to claim 4, wherein the pore pressure controller, the nitrogen seepage pressure controller, the confining pressure controller, the liquid seepage pressure controller, the balance, the gas flowmeter, the axial pressure controller, the telescopic shaft, the seepage outlet pressure sensor, the seepage inlet pressure sensor, a pressure chamber pressure sensor, a pressure chamber temperature sensor, an axial force sensor, the sample base pressure sensor, and the sample cap pressure sensor are connected with a computer.

9. The integrated triaxial shear and seepage experimental device for hydrate-bearing sediments according to claim 4, wherein:

the methane gas cylinder, the nitrogen gas cylinder, the methane pressure adjustment valve, the nitrogen pressure adjustment valve, the gas-liquid separator, the water storage tank, the balance, the gas flowmeter, the gas storage tank, and a computer are not arranged in a constant temperature gas bath; and the sample base gas inlet pores, the seepage inlet pressure sensor, the dowel bar, the upper nut of the dowel bar, the lower nut of the dowel bar, the outer cover of the triaxial pressure chamber, the sample cap seepage pores, the seepage outlet pressure sensor, the methane gas storage tank, the oil tank, the triaxial pressure chamber, the vertical beam of the triaxial instrument, the upper nuts of the transverse beam, the lower nuts the transverse beam, the transverse beam of the triaxial instrument, the base of the triaxial instrument, the axial pressure controller, the upper ejector rod, the pore pressure controller, the confining pressure controller, the nitrogen seepage pressure controller, the nitrogen gas storage tank, the water tank, the liquid seepage pressure controller, and the sample base are arranged in the constant temperature gas bath.

* * * * *